United States Patent [19]

Sakamura

[11] 3,994,259
[45] Nov. 30, 1976

[54] METHOD OF MAKING COCOONS WITH A SOUNDING OBJECT

[76] Inventor: Tomohiko Sakamura, No. 126-1, Fujioka, Fujioka, Gunma, Japan

[22] Filed: June 18, 1975

[21] Appl. No.: 587,882

[30] Foreign Application Priority Data
July 9, 1974 Japan............................ 49-78397

[52] U.S. Cl. ...................................... 119/6; 428/15
[51] Int. Cl.² ........................................ A01K 67/04
[58] Field of Search ................... 119/6; 428/11–17; 156/57, 61; 427/4; 8/94.11

[56] References Cited
UNITED STATES PATENTS
1,704,972  3/1929  Hurst ...................................... 119/6
3,199,245  8/1965  Wenting et al. ........................ 119/6

FOREIGN PATENTS OR APPLICATIONS
139,876  1961  U.S.S.R. .................................. 119/6

Primary Examiner—Hugh R. Chamblee
Assistant Examiner—Peter K. Skiff
Attorney, Agent, or Firm—W. G. Fasse; W. W. Roberts

[57] ABSTRACT

A manufacturing method in which the life cycle of a silkworm, particularly the cocoon forming stage of the silkworm is utilized to insert a sounding object such as a bell in a cocoon formed by the silkworm and thereby to produce a material which is particularly well suited as a material for folk handicrafts personal dress accessories or as a decorative article. Further the cocoon may be colored by the silkworm itself.

8 Claims, 3 Drawing Figures

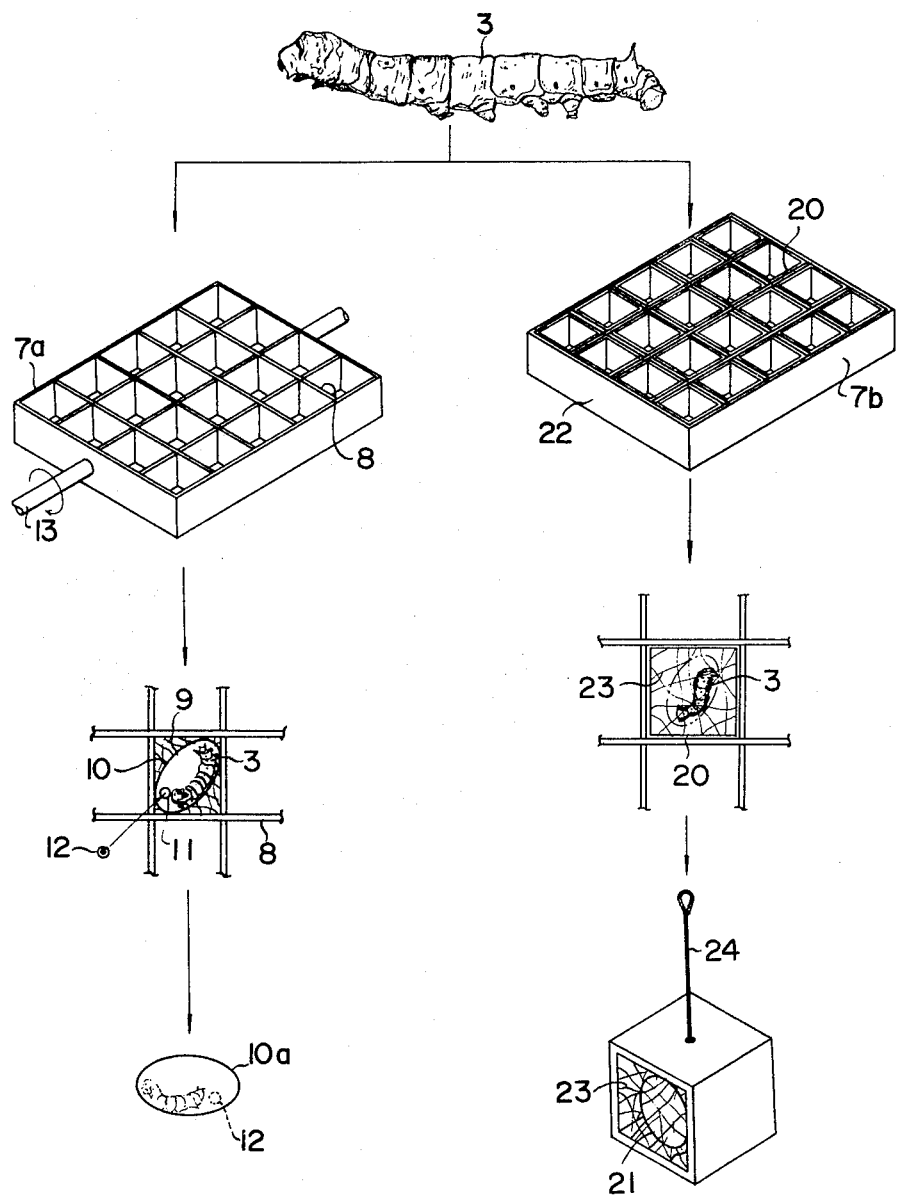

METHOD OF MAKING COCOONS WITH A SOUNDING OBJECT

BACKGROUND OF THE INVENTION

From time immemorial, cocoons formed by silkworms have been highly valued as the source of raw silk for silks and many different technical developments and improvements have been made to obtain silks of high quality and hence high quality raw silk. However, these technical developments and improvements have been directed for the most part to the processing techniques of raw silk such as degumming, weaving and dyeing techniques, and there have been few instances in which the cocoons themselves were valued as materials of folk handicraft articles and industrial art objects. Namely, reality is that there has been developed no technique of processing the cocoon itself to incorporate a sounding object in the cocoon or coloring or imparting the desired color to the cocoon.

However, since the cocoons possess a satisfactory beauty or attractive feature as natural objects, if a sounding device is inserted into the cocoons or the cocoons are colored, it is possible to process the cocoons as such to produce a variety of highly tasteful articles which utilize the properties of the cocoons.

SUMMARY OF THE INVENTION

In view of these requirements, the present invention is directed to the art of processing the cocoons so that the cocoons themselves can be utilized as raw materials of folk handicraft articles, decorative articles and personal dress accessories.

It is an object of the present invention to provide a manufacturing method wherein, by utilizing the habit of silkworm, a sounding object such as a bell is inserted into the cocoon formed by the silkworm to complete the cocoon of a given shape which is best suited as a raw material for making dress accessories or decorative articles.

It is another object of the present invention to provide a manufacturing method of mass producing such cocoons wherein the trace of the insertion of a sounding object into each cocoon is concealed completely to permit the use of the cocoons in many different ways and hence the mass production of beautiful cocoons having graceful luster, is ensured.

It is still another object of the present invention to provide a manufacturing method wherein the habit of silkworms is utilized in such a manner that threads are preliminarily colored as the thread emerges from the body of the silkworms and the cocoons thus produced have a wide range of applications as raw materials for folk handicraft articles and industrial art objects.

The above and other objects, features and advantages of the present invention will become readily apparent from the following detailed description taken in conjunction with the accompanying drawings.

BRIEF DESCRIPTION OF THE DRAWING

FIG. 3 is a diagram showing the typical production steps involved in the manufacturing method according to the present invention.

DESCRIPTION OF THE PREFERRED EMBODIMENTS

Figure 1:
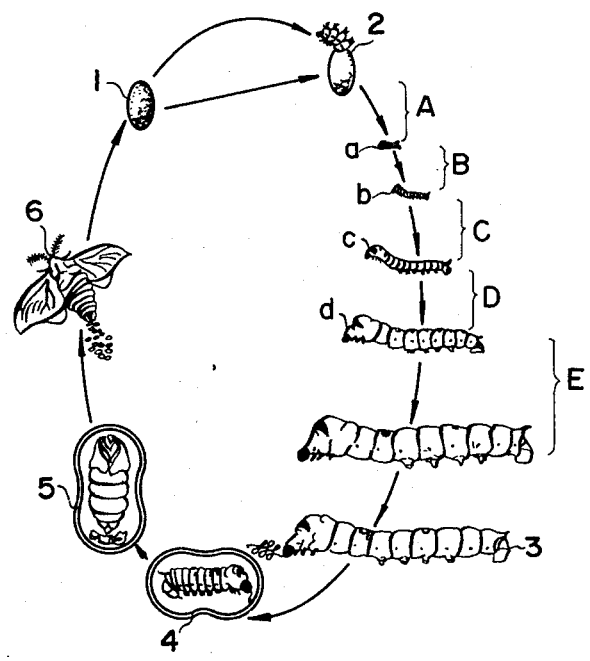
FIG. 1 is a schematic view for explaining the life cycle of silkworm.

FIG. 1 illustrates the typical life cycle of silkworms and this habit of the silkworms is fully utilized in the manufacturing method of this invention. The silkworm passes through the winter as an egg 1 and the egg 1 is hatched as shown at 2 in FIG. 1 in April or May, next year. The larva newly hatched from the egg is usually called a hairy silkworm since it is covered with hair all over the body and it is thus blackish.

As the larva eats mulberry leaves and grows, the larva casts off its old skins four times in about four weeks after which it starts to spin a cocoon. In other words, the silkworm stops eating mulberry leaves and goes into an inactive state one or two days before each of the ecdyses. Since the silkworm appears as if it is in a dormant state, this state is called sleep and the period between the sleeps is called stage. In FIG. 1, symbols A through E indicate in this sequence the first, second, third, fourth and fifth stages, and $a$ through $d$ indicate in this order the first, second, third and fourth sleeps. In about 25 days after the hatching, the silkworm stops eating mulberry leaves, it shrinks slightly and it becomes light brown thus becoming semitransparent. The silkworm in this stage is called an adult silkworm 3 and this adult silkworm starts in a short time to spin a cocoon 4. The adult silkworm forms the cocoon in about 2 to 5 days by spinning the cocoon to wrap or envelop its body and the adult silkworm then casts off its old skin and becomes a pupa 5 in the completed cocoon 4. In about 10 to 15 days thereafter, the pupa casts off its skin and becomes a moth 6 which in turn gets out of the cocoon early in the morning and the female moth copulated in the same day starts laying eggs in the evening of the same day to complete the egg-laying by the next morning.

With the life cycle of silkworms as described above, the method of the present invention makes use of the adult silkworms 3 first. In FIG. 3, numeral 7a designates a spinning nest where the adult silkworms 3 form cocoons. The spinning nest 7a is provided with a large number of frame members 8 so that a large number of the silkworms 3 can simultaneously start spinning the cocoons in the frame members 8.

When the adult silkworms 3 are moved to the spinning nest 7a, each of the adult silkworms 3 crawls about to find a nest of its own and settles in the selected frame member where it spins a cocoon. Thereafter, the silkworm 3 spews out threads which are stretched between the ends of the frame member 8. After the expiration of about 2 hours after the stretching of these threads 9 which serve to hold a cocoon in place when formed, the adult silkworm 3 starts spinning a cocoon proper. In about 3 hours, the cocoon takes a form as shown at 10 in FIG. 3. During this interval, the room temperature is adjusted to about 22° to 25° C. It is of course necessary to ensure a proper ventilation of the room and supply fresh air into the room. In the early period of the cocooning stage, the entire cocoon 10 is made of a thin, transparent outer skin and thus the silkworm 3 in the inside of the cocoon 10 can be positively located from the outside. In this condition, a small hole 11 is formed at one end or the tail portion of the cocoon 10 with an instrument such as a pincette. The size of the hole 11 should preferably be made as small as possible, though it must conform with the size of a sounding object 12 such as a bell. For instance, the diameter of the hole 11 should be less than 8 mm. Of course, care must be taken to prevent damage to the silkworm 3 in the cocoon 10, and the hole 11 is closed with the pincette after the insertion of the sounding object 12 therethrough. A miniature electric bulb of very small size may be inserted into the cocoon 10 in place of the sounding object 12.

Thereafter, the spinning nest 7a is rotated by means of a shaft 13 at intervals of 30 minutes for the duration of about 24 hours so as to prevent the sounding object 12 from sticking to the inside of the cocoon and in this way the cocoon is completed. The silkworm 3 completes the cocoon 10 in about 1 week after the insertion of the sounding object 12 into the cocoon 10 and the hole 11 is completely closed and concealed when completed. At this point, the thus completed cocoon 10a is removed from the spinning nest 7a or rather, from the frame member 8 and the silkworm 3 in the cocoon 10 is killed by means of steam after removing all the undesired fibers, etc. attached to the outside of the cocoon 10.

It will thus be seen from the foregoing description that the method of manufacture of cocoons with a sounding object according to the present invention makes use of the habit of silkworms, that is, their habitual procedure of forming a cocoon in such a manner that a sounding object such as a bell of a suitable size is inserted into the cocoon in the early stage of its formation and the cocoon of a desired shape is obtained while completely closing and concealing the hole used for inserting a sounding object into the cocoon. Therefore, the manufacturing method of this invention has a great utility in that the beautiful cocoons produced are lightweight, satisfactory in strength and rigidity and capable of making a sound, and the cocoons are best suited for use as the raw materials of personal dress accessories such as pendants, necklaces and ear-rings, decorative articles such as desk decorative articles and folk handicraft articles, toys and souvenirs. Moreover, if desired, any desired color may be imparted to the white surface of the cocoons in the manner as will be described hereinafter thus providing a truly versatile raw material, and moreover the fact that these cocoons are produced by employing silkworms which have heretofore been used widely from ancient times makes it possible to produce such cocoons at low cost and in large quantities.

Another embodiment of the manufacturing method of this invention which is designed to provide colored cocoons with a sounding object will now be described. Although it is possible to obtain the desired cocoons by coloring the completed cocoons by any conventional process, a novel feature of the manufacturing method according to the invention is that instead of dyeing the cocoons after their formation, the colored cocoons are obtained upon formation thereof and therefore the novel feature resides in the ingeneous scheme of applying a coloring matter to the silk glands in the body of silkworms. It is essential that the dye or coloring matter used with the method of this invention must be such that the dye has no detrimental effect on the growth and development of the silkworms when it is absorbed into the body of the silkworms. Therefore, the use of vegetable dyes is preferred and the use of petroleum dyes is not desired.

Secondly, the selection of a suitable time for applying coloring matter is very important. Since it is impossible to apply a large quantity of coloring matter to the silkworm at a time, in the method of this invention a sufficient coloring matter is applied to the silkworm in several installments so that an excellent color is imparted to the completed cocoon 10 and the first application of coloring matter is effected before the fourth sleep d of the silkworm, preferably about 2 days (about 45 hours) before the silkworm goes into the fourth sleep. Before the fourth sleep, the larva is not yet secreting in its body any protein which is the raw material of silk yarn and therefore a preliminary application of dye is effected at this stage thus accustoming the larva to the absorption of the applied coloring matter. Various experiments conducted showed that when the application of coloring matter in the fourth sleep was omitted, the resulting coloring of the completed cocoon 10 was unsatisfactory.

There is a very important correlation between the time at which the larva starts secreting in its body, protein which is the raw material of silk yarn and the time at which the coloring matter for producing the colored cocoon is applied to the larva, that is, inaccurate selection of the time for imparting coloring matter tends to result in an unsatisfactory coloring of the completed cocoon 10 and has the danger of producing detrimental effects on the growth of the silkworm. Therefore the time at which silkworms start secreting protein will now be explained. The protein which is the raw material of the silk yarn consists of fibroin and sericin, and the protein is stored in the silk glands in the body of silkworms. The silk glands are divided into the fore silk glands which are mere passages for spinning out silk threads, the mid silk glands for secreting gelatinous sericin that envelops the silk filaments and the rear silk glands for secreting the fibroin which is the source of the silk yarn. When the larva enters into the fourth sleep d, the protein or the raw material of the silk yarn is gradually secreted and stored in the mid and rear silk glands, and in the fifth stage E which follows the fourth ecdysis after the fourth sleep the production activity of protein in the body of the larva is rapidly boosted. Consequently, the larva has the greatest appetite continuously eating a large quantity of mulberry leaves and the larva now matures into an adult silkworm 3. For this reason, according to the method of this invention, the required coloring matter is applied in several installments (3 to 4 times) during the time interval between the time when the protein or the raw material of the silk yarn is most actively secreted and stored in the body of the larvae, i.e., the fifth stage after the fourth sleep and the time of moving the larvae to the spinning nest. Experiments conducted showed that the most satisfactory coloring of the cocoon was accomplished when the second dye application was effected on the second day in the fifth stage of the larva and the coloring matter was applied for the third time on the 4th day in the fifth stage of the larva.

While the coloring matter is applied first before the fourth sleep of larvae and it is also applied several times in the fifth stage of the larvae but before their movement to the spinning nest, the coloring matter must be applied exactly at the stomata of larvae through which the larvae breath, otherwise practically no coloring matter may be absorbed into the silk glands. It should be noted, however, that all the stomata are not equally effective. That is, while the silkworm has 8 breathing holes on each side of its abdomen, only the breathing holes on either of the two sides excepting the foremost one, that is, only 7 of the breathing holes receive the coloring matter. The reason is that the foremost one of the light breathing holes on each side is associated with the fore silk glands which have no direct bearing on the formation and secretion of the protein which is the raw material of the silk yarn and therefore the application of the coloring matter to the foremost breathing hole has no bearing on the coloring effect. On the other hand, the breathing holes on one side alone are used because the application of coloring matter to all the breathing holes on both sides temporarily causes the silkworms to breath with difficulty and tend to weaken the silkworms and thus to impede the formation of high quality cocoons. Consequently, each of the above-mentioned several applications of coloring matter is effected at the same breathing holes. The application of coloring matter may be accomplished with a writing brush or paintbrush.

In this way, when the coloring matter is applied several times to the breathing holes associated with the mid and rear silk glands, a satisfactory amount of the coloring matter is absorbed into the body, particularly into the silk glands where it is assimilated with the protein. The adult silkworms 3 matured in this way are moved to the spinning nest where they spin cocoons in the respective frame members. The silkworms which have finished the fifth stage E become the adult silkworms 3 and in this stage of their development the adult silkworms 3 do not have as much appetite as before and the production of the raw material of the silk yarn in their bodies has already come to an end. Consequently, the adult silkworms 3 now solely crawl about over the spinning nest seeking suitable places where they can safely settle in for cocooning and the adult silkworms eventually settle in the respective frame members in the spinning nest where they first stretch supporting threads 9 and then the silkworms spin cocoons 10 by spewing out the threads in the shape of S or 8 while shaking their heads. Since the threads thus spewed out were already colored, the supporting threads 9 and the cocoons 10 have very graceful luster directly reflecting the coloring of the coloring matter. During this cocooning period, a small hole 11 may be formed in the cocoon 10 so that a sounding object 12 or the like may be inserted into the cocoon 10 in the manner described earlier. The shape and structure of the illustrated spinning nest are illustrative only and many changes and modifications may be made to the spinning nest.

Finally, the silkworms 3 in the cocoons 10 are killed by means of steam to complete the cocoons of the desired color. In this case, since the cocoons are made of the preliminarily colored threads, the beautiful colored cocoons with the sounding object 12 which are not obtainable by coloring the formed cocoons are manufactured.

Figure 2:
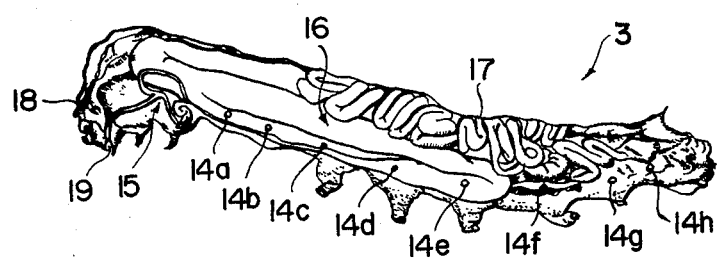
FIG. 2 is a sectional view showing the essential parts of the internal organs of a matured silkworm.

Referring now to FIGS. 2 and 3, the following example described in greater detail the production of the cocoons in accordance with the manufacturing method of this invention. While, in the following example, no sounding object was inserted into the cocoon, it is of course possible to easily insert any sounding object into the cocoon in the manner described above.

EXAMPLE

A silkworm egg 1 was hatched to obtain a hairy worm, and when the hairy worm grew and became an adult silkworm 3, a red dye was applied by means of a paintbrush to breathing holes 14b to 14h on one abdominal side of the silkworm 3, no dye is applied to the foremost breathing hole 14a. The time of the first application was 45 hours before the fourth sleep d, the second application was made on the second day in the fifth stage E following the fourth sleep and the third application was effected on the 3rd day in the fifth stage. In FIG. 2, numeral 15 designates the fore silk gland, 16 the mid silk gland, 17 the rear silk gland, 18 the head, 19 the spinning port.

The adult silkworms 3 were then moved to a double shell spinning nest 7b where the silkworms 3 settled in the suitably selected inner frame members 20 to start spinning cocoons and they completed cocoons 21 in 3 days. The inner frame members 20 with the cocoons 21 were removed from an outer frame member 22 and then the silkworms in the cocoons were killed by means of steam in a conventional manner. Each of the inner frame member 20 was made of a wallpaper with patterns and the outer frame member 22 was made of an ordinary cardboard, with both the inner and outer frame members 20 and 22 formed into a square shape.

When the silkworms 3 completed the cocoons, the red cocoon 21 held in position by graceful red colored supporting threads 23 was formed in each of the inner frame members 20 made of the beautifully patterned wallpaper. By attaching a cord 24 to the inner frame member 20, a fitting decorative article was obtained.

It will thus be seen from the foregoing description that in accordance with the present invention, instead of the raw silk for silks, the cocoons themselves and sometimes the cocoons integrally incorporated in their respectively cocooning inner frame members can be used as the raw materials of folk handicraft articles and industrial art objects. While this alone permits the utilization of the various properties possessed by the cocoons, the fact that the threads spewed out by silkworms can be preliminarily colored as desired before the formation of the cocoons also ensures that not only the supporting threads stretched in the inner frame members but also the cocoons themselves have an excellent coloring which gives a person the similar impression as the natural color and the thus obtained colored cocoons with the preliminarily inserted sounding objects make them really tasteful articles. In addition, by virtue of the fact that the insertion of sounding objects and coloring operations are effected by utilizing the habit of silkworms in their growth and development, particularly the coloring operations are effected by causing the silkworms to absorb the desired coloring matter through their breathing holes during the suitably selected periods when the silkworms start secreting the protein or the raw material of silk by the inner silk glands and when this secreting activity reaches the maximum, it is possible to easily and positively manufacture a large number of the colored and well-shaped cocoons without any detrimental effects on the growth of the silkworms. Especially, the use of a double shell type spinning nest has the effect of producing cocoons which are best suited as such for use as the raw materials of folk handicraft articles as well as industrial art objects. Thus, the present invention has a very great utility.

Having described my invention, what I claim as new and desire to secure by Letters Patent is:

1. A method of making a cocoon with a sounding object comprising the steps of: moving an adult silkworm to a spinning nest and forming a cocoon; forming a hole in a tail portion of said cocoon in an early period of the formation thereof; inserting a sounding object such as a bell into said cocoon through said hole; completing the formation of said cocoon while rotating said spinning nest; removing said cocoon from said spinning nest and killing said silkworm in said cocoon by steam.

2. The method according to claim 1, wherein before the movement of said adult silkworm to said spinning nest, a suitable amount of a coloring matter is preliminarily applied to the breathing holes associated with the mid and rear glands of said silkworm at a time before said silkworm sleeps for the fourth time, and repeatedly applying said coloring matter to said breathing holes during a time period between a fifth stage of said silkworm following said fourth sleep and a time at which said silkworm is moved to said spinning nest so as to allow said coloring matter to be fully absorbed by said mid and rear silk glands.

3. A method of making a colored cocoon comprising the steps of: preliminarily applying a suitable amount of a coloring matter to the breathing holes associated with the mid and rear silk glands of a silkworm at a time before said silkworm sleeps for the fourth time; applying said coloring matter several times to said breathing holes during a time period between a fifth stage of said silkworm following said fourth sleep and a time at which said silkworm is moved to a spinning nest so so as to allow said coloring matter to be fully absorbed by said mid and rear silk glands; causing said adult silkworm to spin a cocoon in said spinning nest; and killing said silkworm by steam in said cocoon after the completion of the cocoon.

4. A decorative cocoon produced by moving an adult silk worm to a spinning nest to permit the silk worm to form the cocoon, making a hole in a portion of said cocoon in an early period of the formation thereof, inserting an extraneous device into said cocoon through said hole, permitting the silk worm to complete the formation of the cocoon while rotating said spinning nest, removing said cocoon from said spinning nest and killing said silk worm therein, whereby said extraneous device remains implanted in said cocoon shell.

5. The decorative cocoon according to claim 4, wherein said extraneous device is a sounding device.

6. The decorative cocoon according to claim 5, wherein said sounding device is a bell.

7. A decorative cocoon produced by applying a suitable amount of coloring matter to the breathing holes associated with the mid and rear silk glands of a silk worm at a time before said silk worm sleeps for the fourth time, applying said coloring matter several times to said breathing holes during a time period between a fifth stage of said silk worm following said fourth sleep and a time at which said silk worm is moved to a spinning nest so as to allow said coloring matter to be fully absorbed by said mid and rear silk glands, causing said adult silk worms to spin said cocoon in said spinning nest and killing said silk worm in said cocoon after the completion of the cocoon, whereby the artificial coloring becomes an inherent part of the thread which the silk worm forms into said cocoon.

8. The decorative cocoon according to claim 7, further comprising an extraneous device implanted in said shell.

* * * * *